US009248330B1

(12) United States Patent
Ghanem (10) Patent No.: US 9,248,330 B1
(45) Date of Patent: Feb. 2, 2016

(54) LEG STRENGTHENING DEVICE AND ASSOCIATED USE THEREOF

(71) Applicant: Nybil Ghanem, S. Plainfield, NH (US)

(72) Inventor: Nybil Ghanem, S. Plainfield, NH (US)

(*) Notice: Subject to any disclaimer, the term of this patent is extended or adjusted under 35 U.S.C. 154(b) by 0 days.

(21) Appl. No.: 14/495,879

(22) Filed: Sep. 24, 2014

Related U.S. Application Data

(60) Provisional application No. 61/881,465, filed on Sep. 24, 2013.

(51) Int. Cl.
*A63B 21/00* (2006.01)
*A63B 21/008* (2006.01)

(52) U.S. Cl.
CPC ............ *A63B 21/008* (2013.01); *A63B 2225/62* (2013.01)

(58) Field of Classification Search
USPC ....................................................... 482/1–148
See application file for complete search history.

(56) References Cited

U.S. PATENT DOCUMENTS

| 5,137,504 | A | * | 8/1992 | Mangini | A61H 1/0244 482/131 |
| 5,277,681 | A | * | 1/1994 | Holt | A61H 1/02 482/112 |
| 5,518,482 | A | * | 5/1996 | Hsieh | A63B 21/055 482/130 |
| 7,485,078 | B1 | * | 2/2009 | Chen | A63B 22/20 482/121 |
| 7,828,700 | B1 | * | 11/2010 | Tsai | A63B 21/0552 482/121 |

* cited by examiner

*Primary Examiner* — Stephen Crow (57) ABSTRACT

A leg exercising apparatus includes a back support having a brace connected thereto, a seat support attached to the brace and spaced from the back support, a plurality of deformably flexible leg supports having proximal ends pivotally coupled to the seat support, and a plurality of foot supports pivotally coupled to distal ends of the leg supports, respectively. In this manner, the leg supports are independently pivoted along arcuate leg support paths defined about mutually exclusive leg fulcrum axes located at the proximal ends of the leg supports, respectively. Similarly, the foot supports are independently pivoted along arcuate foot support paths defined about mutually exclusive foot fulcrum axes located at the distal ends of the leg supports, respectively.

17 Claims, 5 Drawing Sheets

LEG STRENGTHENING DEVICE AND ASSOCIATED USE THEREOF

CROSS REFERENCE TO RELATED APPLICATIONS

This application claims the benefit of U.S. Provisional Application No. 61/881,465 filed Sep. 24, 2013, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to exercise devices and, more particularly, to mechanical leg braces, specially designed for individuals with lower extremity disabilities that are configured to assist in the straightening and strengthening of leg muscles thereby providing an effective means for preventing atrophy, and improving strength and mobility in their legs.

Prior Art

In certain diseases, such as poliomyelitis cases, or after certain operations, the legs of the patient frequently become temporarily weakened or paralyzed, and in the treatment of such cases the weakened leg or foot must be supported in a suitable brace which will allow the patient to duplicate the natural movements of the foot and leg during walking, whereby the physical therapist will be able to assist the patient in recovering the greatest degree of mobility of the leg and foot, and also allows the therapist to train the patient to use the brace. It also is desirable that the foot be permitted as much freedom of movement as possible, particularly in the case known as drop-foot, to allow exercise of the paralyzed or weakened muscles. Such action is of great benefit as it aids in restoring the muscles, it promotes proper circulation of the blood in the temporarily or permanently paralyzed limb and helps to prevent atrophy of the limb.

Accordingly, a need remains for mechanical leg braces in order to overcome at least one prior art shortcoming. The exemplary embodiment(s) satisfy such a need by providing mechanical leg braces, specially designed for individuals with lower extremity disabilities that are configured to assist in the straightening and strengthening of leg muscles that is convenient and easy to use, lightweight yet durable in design, versatile in its applications, and designed for providing an effective means for preventing atrophy, and improving strength and mobility in their legs.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a leg strengthening device. These and other objects, features, and advantages of the non-limiting exemplary embodiment(s) are provided by a leg exercising apparatus including a back support having a brace connected thereto, a seat support attached to the brace and spaced from the back support, a plurality of deformably flexible leg supports having proximal ends pivotally coupled to the seat support, and a plurality of foot supports pivotally coupled to distal ends of the leg supports, respectively. In this manner, the leg supports are independently pivoted along arcuate leg support paths defined about mutually exclusive leg fulcrum axes located at the proximal ends of the leg supports, respectively. Similarly, the foot supports are independently pivoted along arcuate foot support paths defined about mutually exclusive foot fulcrum axes located at the distal ends of the leg supports, respectively.

In a non-limiting exemplary embodiment, the plurality of leg supports include a first leg support member pivotally hinged to the seat support and rotated about a first one of the arcuate foot support paths, and a second leg support member having a proximal end pivotally hinged to the seat support and rotated about a second one of the arcuate foot support paths.

In a non-limiting exemplary embodiment, each of the first leg support member and the second leg support member includes an outer layer extending along an entire longitudinal length of the first leg support member. In addition, a mesh layer is in operable communication with the outer layer and extending along an entire longitudinal length thereof. Notably, the mesh layer is located along curvilinear surface of the outer layer.

In a non-limiting exemplary embodiment, each of the first leg support member and the second leg support member further includes a plurality of straps affixed to opposing longitudinal edges of the mesh layer. Associated pairs of the straps are selectively affixed and detached thereby maintaining the first leg support member and the second leg support member at substantially stable positions, respectively.

In a non-limiting exemplary embodiment, the outer layer includes a cavity extending along an entire longitudinal length thereof, respectively. A tensioning implement is in operable communication with the cavity and the mesh layer, and a pressure-releasing implement is in operable communication with the cavity and the mesh layer.

In a non-limiting exemplary embodiment, the tensioning implement is an air pump affixed to the outer layer and the releasing implement is an air valve affixed to the outer layer. Thus, the air pump selectively introduces air-pressure into the cavity and thereby causes the mesh layer to compress while maintaining a substantially U-shaped cross-section. Further, the air valve selectively discharges air-pressure out from the cavity and thereby causes the mesh layer to decompress while maintaining the substantially U-shaped cross-section.

In a non-limiting exemplary embodiment, the mesh layer is located exterior of the cavity and positioned along an outer wall of the outer layer.

In a non-limiting exemplary embodiment, the mesh layer is housed interior of the cavity.

The present disclosure further includes a method of utilizing a leg exercising apparatus. Such a method includes the steps of: providing a back support having a brace connected thereto; providing and attaching a seat support to the brace such that the seat support is spaced from the back support; providing a plurality of deformably flexible leg supports having proximal ends; pivotally coupling the proximal ends to the seat support; providing and pivotally coupling a plurality of foot supports to distal ends of the leg supports, respectively; independently pivoting the leg supports along arcuate leg support paths defined about mutually exclusive leg fulcrum axes located at the proximal ends of the leg supports, respectively; and independently pivoting the foot supports along arcuate foot support paths defined about mutually exclusive foot fulcrum axes located at the distal ends of the leg supports, respectively.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary emboidment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to generally in FIGS. 1-4 and is/are intended to provide a mechanical leg braces (collectively as leg exercising apparatus 10), specially designed for individuals with lower extremity disabilities that are configured to assist in the straightening and strengthening of leg muscles thereby providing an effective means for preventing atrophy, and improving strength and mobility in their legs. It should be understood that the exemplary embodiment may be used to strengthen a variety of leg types, and should not be limited to any particular type of a user leg described herein.

Referring to FIGS. 1-4 in general, a leg exercising apparatus 10 includes a back support 11 having a brace 12 connected thereto, a seat support 13 attached to the brace 12 and spaced from the back support 11, a plurality of deformably flexible leg supports 14, 24 having proximal ends 15, 25 pivotally coupled to the seat support 13, and a plurality of foot supports 16, 26 pivotally coupled to distal ends 34, 35 of the leg supports 14, 24, respectively. In this manner, the leg supports 14, 24 are independently pivoted along arcuate leg support paths 17, 18 defined about mutually exclusive leg fulcrum axes 19, 20 located at the proximal ends 15, 25 of the leg supports 14, 24, respectively. Similarly, the foot supports 16, 26 are independently pivoted along arcuate foot support paths 30, 31 defined about mutually exclusive foot fulcrum axes 32, 33 located at the distal ends 34, 35 of the leg supports 14, 24, respectively.

In a non-limiting exemplary embodiment, the plurality of leg supports 14, 24 include a first leg support member 36 having a proximal end 15 pivotally hinged 75 to the seat support 13 and rotated about a first one of the arcuate foot support paths 30, 31, and a second leg support having a proximal end 25 pivotally hinged (same as hinge 75 in FIG. 3a) to the seat support 13 and rotated about a second one of the arcuate foot support paths 30, 31.

In a non-limiting exemplary embodiment, each of the first leg support member 36 and the second leg support member 37 includes an outer layer 40, 60 extending along an entire longitudinal length thereof, respectively. In addition, a mesh layer 41, 61 is in operable communication with the outer layer 40, 60 and extending along an entire longitudinal length thereof. Notably, the mesh layer 41, 61 is located along curvilinear surface of the outer layer 40, 60.

In a non-limiting exemplary embodiment, the first leg support member 36 and the second leg support member 37 further includes a plurality of straps 42, 43, respectively, affixed to opposing longitudinal edges of the mesh layer 41, 61, respectively. Associated pairs of the straps 42, 43 are selectively affixed and detached thereby maintaining the first leg support member 36 and the second leg support member 37 at substantially stable positions, respectively.

In a non-limiting exemplary embodiment, each outer layer 40, 60 includes a cavity 44, 64 extending along an entire longitudinal length thereof, respectively. A tensioning implement 45, 65 is in operable communication with the cavity 44, 64 and the mesh layer 41, 61, respectively, and a pressure-releasing implement 46, 66 is in operable communication with the cavity 44, 64 and the mesh layer 41, 61, respectively.

In a non-limiting exemplary embodiment, the tensioning implement 45, 65 is an air pump 47, 67 affixed to the outer layer 40, 60 and the releasing implement is an air valve 48, 68 affixed to the outer layer 40, 60. Thus, the air pump 47, 67 selectively introduces air-pressure into the cavity 44, 64 and thereby causes the mesh layer 41, 61 to compress while maintaining a substantially U-shaped cross-section. Further, the air valve 48, 68 selectively discharges air-pressure out from the cavity 44, 64 and thereby causes the mesh layer 41, 61 to decompress while maintaining the substantially U-shaped cross-section.

In a non-limiting exemplary embodiment, the mesh layer 41, 61 is located exterior of the cavity 44, 64 and positioned along an outer wall of the outer layer 40, 60.

Figure 1:
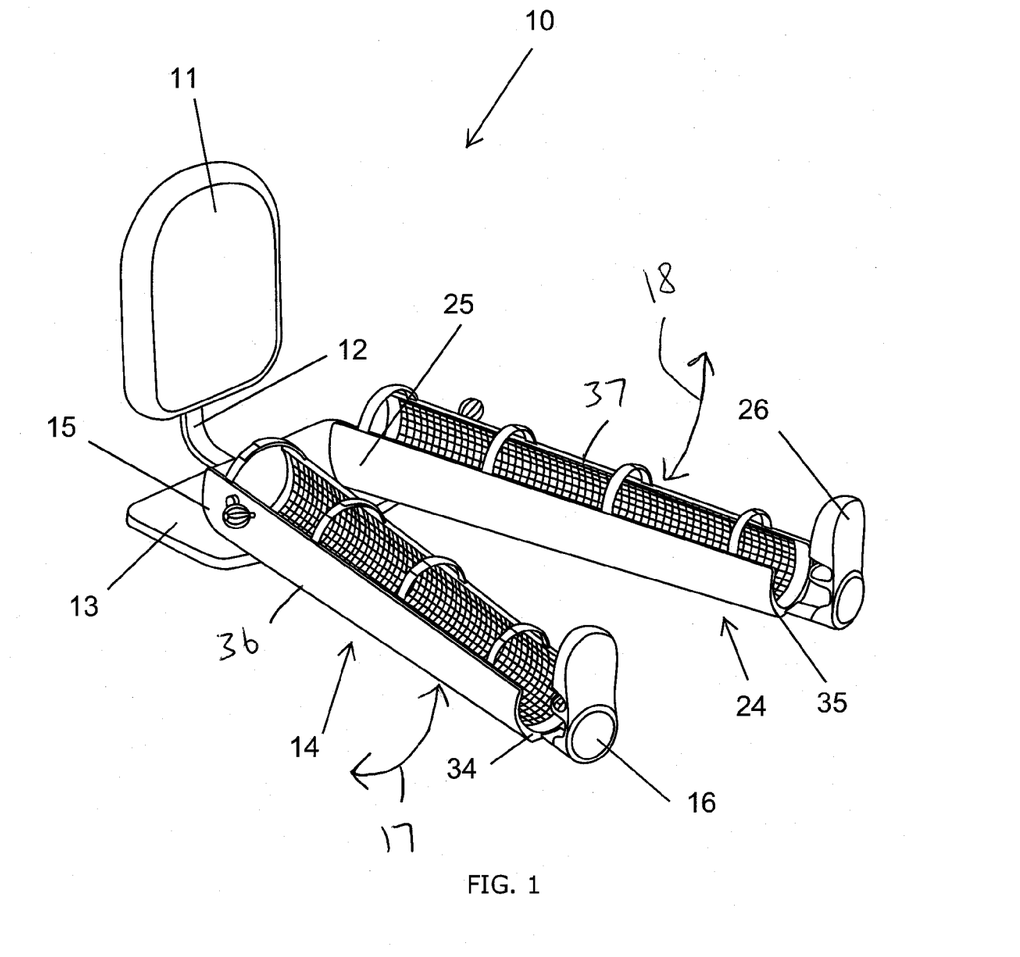
FIG. 1 is a perspective view of a leg strengthening device, in accordance with a non-limiting exemplary embodiment.
Figure 2:
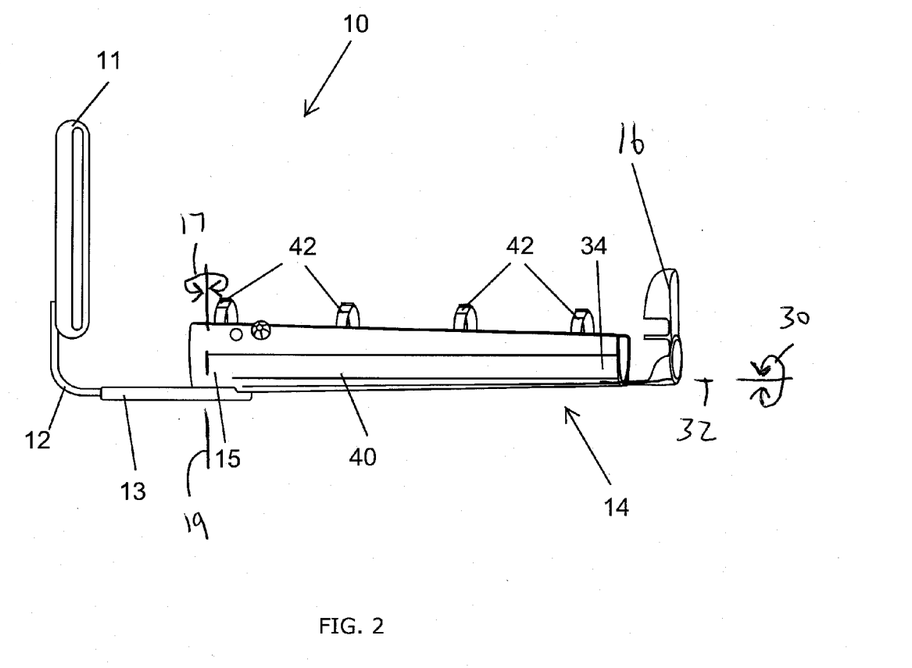
FIG. 2 is a side elevational view of the leg strengthening device shown in FIG. 1.
Figure 3:
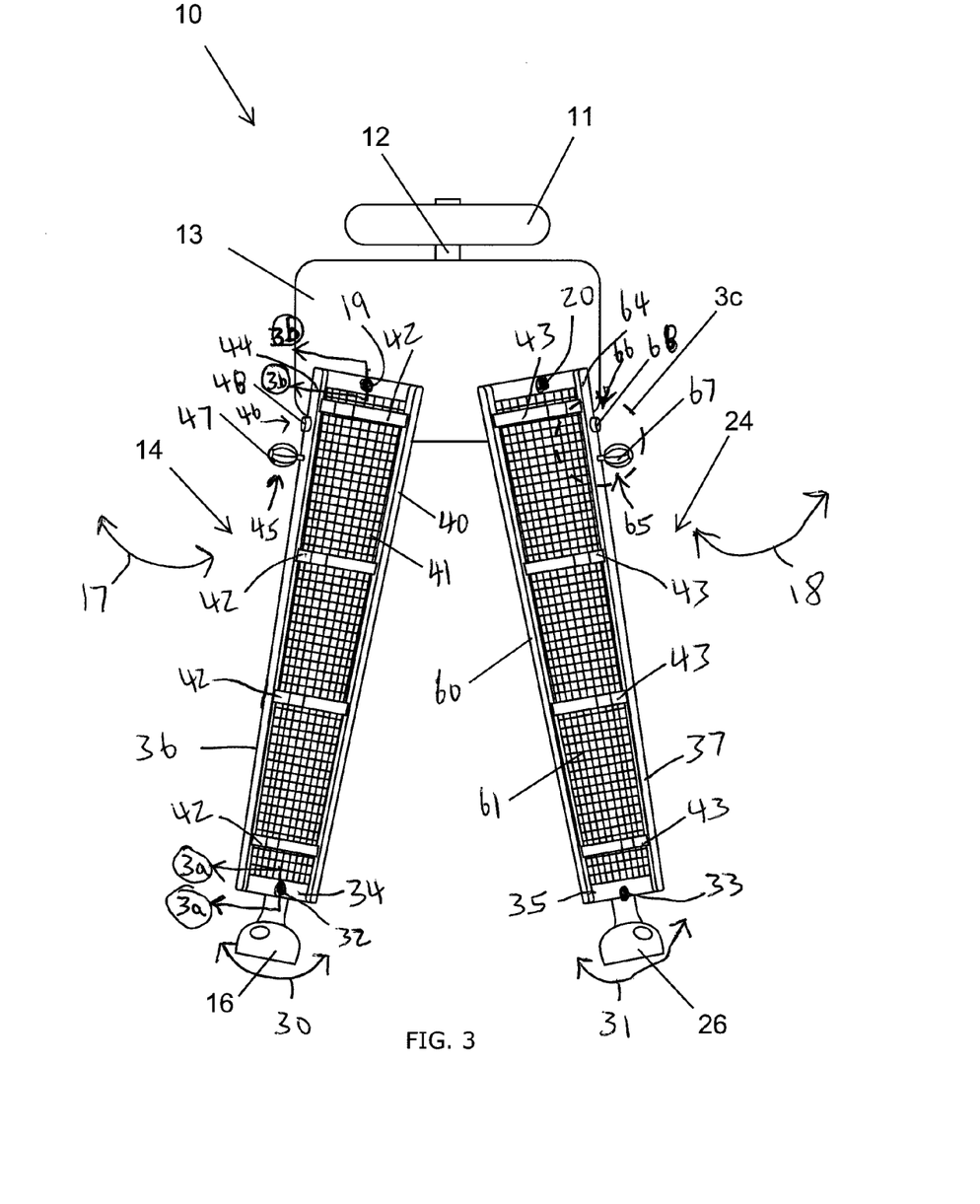
FIG. 3 is a top plan view of the leg strengthening device shown in FIG. 1.
Figure 3A:
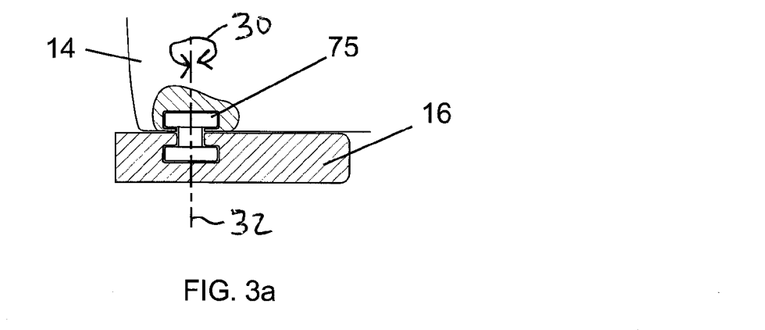
FIG. 3a is an enlarged cross-sectional view taken along line 3a-3a in FIG. 3.
Figure 3B:
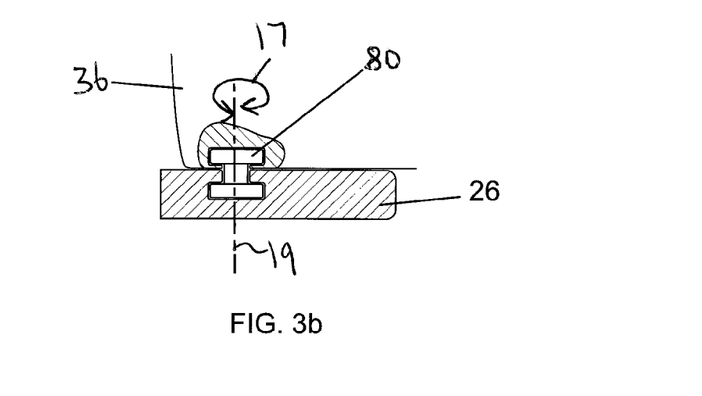
FIG. 3b is an enlarged cross-sectional view taken along line 3b-3b in FIG. 3.
Figure 3C:
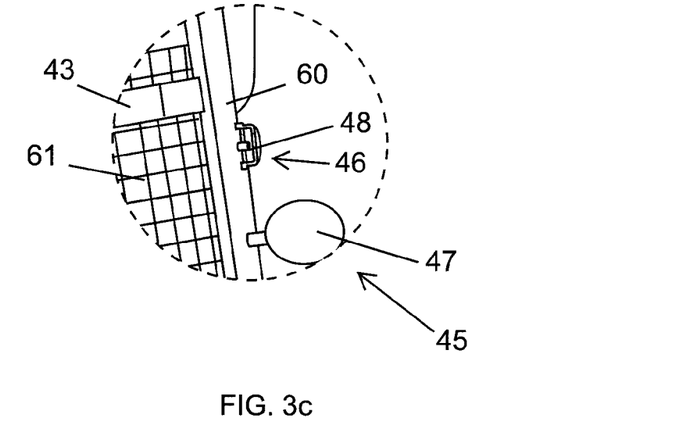
FIG. 3c is an enlarged view of section 3c.
Figure 4:
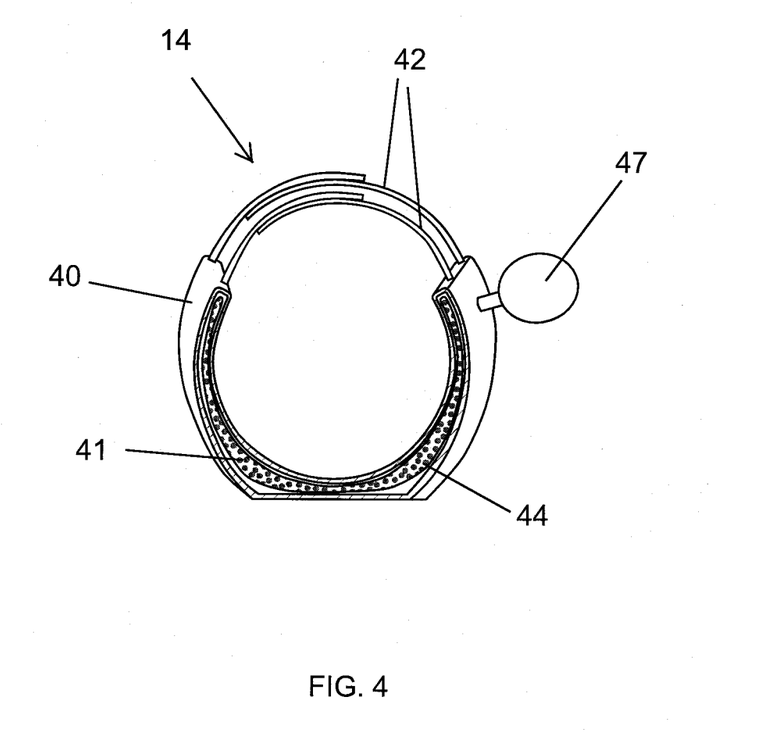
FIG. 4 is an enlarged cross-sectional view showing an alternate embodiment wherein the mesh layer is housed within the cavity of the outer layer.

In a non-limiting exemplary embodiment, the mesh layer 41, 61 is housed interior of the cavity 44, 64.

The present disclosure further includes a method of utilizing a leg exercising apparatus 10. Such a method includes the steps of: providing a back support 11 having a brace 12 connected thereto; providing and attaching a seat support 13 to the brace 12 such that the seat support 13 is spaced from the back support 11; providing a plurality of deformably flexible leg supports 14, 24 having proximal ends 15, 25; pivotally coupling the proximal ends 15, 25 to the seat support 13; providing and pivotally coupling a plurality of foot supports 16, 26 to distal ends 34, 35 of the leg supports 14, 24, respectively; independently pivoting the leg supports 14, 24 along arcuate leg support paths 17, 18 defined about mutually exclusive leg fulcrum axes 19, 20 located at the proximal ends 15, 25 of the leg supports 14, 24, respectively; and independently pivoting the foot supports 16, 26 along arcuate foot support paths 30, 31 defined about mutually exclusive foot fulcrum axes 32, 33 located at the distal ends 34, 35 of the leg supports 14, 24, respectively.

In a non-limiting exemplary embodiment, the leg exercising apparatus 10 could be fashioned as a series of hinged metal rods that are able to force movement of the legs while also conforming to the basic leg shape. These rods would be connected via a series of VELCRO® (or similar) straps 42, 43, which would also facilitate secure attachment to the legs. Additionally, a handy strap to wrap around the lower back would be provided for optimal security of the leg exercising apparatus 10 while the system is worn. Covering the legs from hip to heel, the leg exercising apparatus 10 would culminate in a pair of open foot holders 16, 26 at the distal end of each leg support member 36, 37, respectively.

A collection of wire connectors (e.g., mesh layer 41, 61) would be fed through the extremities of the leg exercising apparatus 10, and calibrated to activate a proximal twist knob that would be employed to adjust the mesh layers 41, 61 into a straight line, thus straightening the legs. For applying therapeutic pressure to the leg muscles, each leg support 14, 24 would contain a device referred to by the inventor as a "bike" lever, or a component that when pressed or turned would tighten the mesh layers 41, 61 around the legs at a pressure level that is most comfortable for the wearer. As envisioned, the leg exercising apparatus 10 could be worn and used while sitting, and while engaging in a monitored therapy regimen of walking.

Because this product is an exercising apparatus 10, the inventor suggests that the wearer be fitted with this device by an orthopedic doctor or other medical professional to ensure proper fitting on the legs. In this manner, low income patients with disabilities could also reap the benefits offered by use of this device.

Fully realized, a product such as the leg exercising apparatus 10 could offer numerous benefits and advantages. For example, the leg exercising apparatus 10 could provide mobility-impaired individuals with a simple yet effective therapeutic device. Wearable leg supports 14, 24 designed to both straighten and strengthen lower extremities, the leg exercising apparatus 10 could help prevent muscles from becoming atrophied, a very real risk for individuals who are disabled.

Strapped on and activated while lying in bed, watching television, moving around in a wheelchair or on crutches, or during physical therapy, the leg exercising apparatus 10 could be easily adjusted to concentrate on the thighs, knees, calves, hamstrings, or all of the above at the same time. In this manner, the stability provided by the straightening as well as the strengthening power of pressure could keep leg muscles in good shape. Thus, it is the inventor's intention that the leg exercising apparatus 10 provide disabled individuals with a more improved quality of life, which includes the possibility that the product would assist some of these patients in recovering some of their ability to walk.

Whether employed in the home setting or during physical therapy sessions, the versatile leg exercising apparatus 10, upon development, should be well received by all who experience lower extremity disability, both permanent and temporary, and by the doctors and therapists who treat them.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A leg exercising apparatus comprising:
    a back support having a brace connected thereto;
    a seat support attached to said brace;
    a plurality of leg supports having proximal ends in communication with said seat support; and
    a plurality of foot supports in communication with distal ends of said leg supports, respectively;
    wherein said leg supports are independently pivoted along arcuate leg support paths defined about mutually exclusive leg fulcrum axes located at said proximal ends of said leg supports, respectively;
    wherein said foot supports are independently pivoted along arcuate foot support paths defined about mutually exclusive foot fulcrum axes located at said distal ends of said leg supports, respectively.

2. The leg exercising apparatus of claim 1, wherein said plurality of leg supports comprise:
    a first leg support member pivotally hinged to said seat support and rotated about a first one of said arcuate foot support paths; and
    a second leg support member having a proximal end pivotally hinged to said seat support and rotated about a second one of said arcuate foot support paths.

3. The leg exercising apparatus of claim 2, wherein each of said first leg support member and said second leg support member comprises:
    an outer layer extending along an entire longitudinal length thereof; and
    a mesh layer in operable communication with said outer layer and extending along an entire longitudinal length thereof;
    wherein said mesh layer is located along curvilinear surface of said outer layer.

4. The leg exercising apparatus of claim 3, wherein each of said first leg support member and said second leg support member further comprises:
    a plurality of straps affixed to opposing longitudinal edges of said mesh layer;
    wherein associated pairs of said straps are selectively affixed and detached thereby maintaining said first leg support member and said second leg support member at substantially stable positions, respectively.

5. The leg exercising apparatus of claim 4, wherein said outer layer comprises:
    a cavity extending along an entire longitudinal length thereof, respectively;
    a tensioning implement in operable communication with said cavity and said mesh layer; and
    a pressure-releasing implement in operable communication with said cavity and said mesh layer.

6. The leg exercising apparatus of claim 5, wherein said tensioning implement is an air pump affixed to said outer layer and said releasing implement is an air valve affixed to said outer layer;
    wherein said air pump selectively introduces air-pressure into said cavity and thereby causes said mesh layer to compress while maintaining a substantially U-shaped cross-section;
    wherein said air valve selectively discharges air-pressure out from said cavity and thereby causes said mesh layer to decompress while maintaining said substantially U-shaped cross-section.

7. The leg exercising apparatus of claim 6, wherein said mesh layer is located exterior of said cavity and positioned along an outer wall of said outer layer.

8. The leg exercising apparatus of claim 6, wherein said mesh layer is housed interior of said cavity.

9. A leg exercising apparatus comprising:
    a back support having a brace connected thereto;
    a seat support attached to said brace and spaced from said back support;
    a plurality of leg supports having proximal ends pivotally coupled to said seat support; and
    a plurality of foot supports pivotally coupled to distal ends of said leg supports, respectively;
    wherein said leg supports are independently pivoted along arcuate leg support paths defined about mutually exclusive leg fulcrum axes located at said proximal ends of said leg supports, respectively;
    wherein said foot supports are independently pivoted along arcuate foot support paths defined about mutually exclusive foot fulcrum axes located at said distal ends of said leg supports, respectively;
    wherein said leg supports are deformably flexible.

10. The leg exercising apparatus of claim 9, wherein said plurality of leg supports comprise:
    a first leg support member pivotally hinged to said seat support and rotated about a first one of said arcuate foot support paths; and
    a second leg support member having a proximal end pivotally hinged to said seat support and rotated about a second one of said arcuate foot support paths.

11. The leg exercising apparatus of claim 10, wherein each of said first leg support member and said second leg support member comprises:
    an outer layer extending along an entire longitudinal length thereof; and
    a mesh layer in operable communication with said outer layer and extending along an entire longitudinal length thereof;

wherein said mesh layer is located along curvilinear surface of said outer layer.

12. The leg exercising apparatus of claim 11, wherein each of said first leg support member and said second leg support member further comprises:
- a plurality of straps affixed to opposing longitudinal edges of said mesh layer;
- wherein associated pairs of said straps are selectively affixed and detached thereby maintaining said first leg support member and said second leg support member at substantially stable positions, respectively.

13. The leg exercising apparatus of claim 12, wherein said outer layer comprises:
- a cavity extending along an entire longitudinal length thereof, respectively;
- a tensioning implement in operable communication with said cavity and said mesh layer; and
- a pressure-releasing implement in operable communication with said cavity and said mesh layer.

14. The leg exercising apparatus of claim 13, wherein said tensioning implement is an air pump affixed to said outer layer and said releasing implement is an air valve affixed to said outer layer;
- wherein said air pump selectively introduces air-pressure into said cavity and thereby causes said mesh layer to compress while maintaining a substantially U-shaped cross-section;
- wherein said air valve selectively discharges air-pressure out from said cavity and thereby causes said mesh layer to decompress while maintaining said substantially U-shaped cross-section.

15. The leg exercising apparatus of claim 14, wherein said mesh layer is located exterior of said cavity and positioned along an outer wall of said outer layer.

16. The leg exercising apparatus of claim 14, wherein said mesh layer is housed interior of said cavity.

17. A method of utilizing a leg exercising apparatus, said method comprising the steps of:
- providing a back support having a brace connected thereto;
- providing and attaching a seat support to said brace such that said seat support is spaced from said back support;
- providing a plurality of deformably flexible leg supports having proximal ends;
- pivotally coupling said proximal ends to said seat support;
- providing and pivotally coupling a plurality of foot supports to distal ends of said leg supports, respectively;
- independently pivoting said leg supports along arcuate leg support paths defined about mutually exclusive leg fulcrum axes located at said proximal ends of said leg supports, respectively; and
- independently pivoting said foot supports along arcuate foot support paths defined about mutually exclusive foot fulcrum axes located at said distal ends of said leg supports, respectively.

* * * * *